(12) United States Patent
Cropper et al.

(10) Patent No.: US 9,095,531 B2
(45) Date of Patent: Aug. 4, 2015

(54) ANTIPERSPIRANT COMPOSITIONS

(75) Inventors: Martin Peter Cropper, Bebington (GB); Kevin Ronald Franklin, Bebington (GB); Louise Jannette Roberts, Bebington (GB)

(73) Assignee: Conopco, Inc., AG West, S. Wing Englewood Cliffs, NJ (US)

( * ) Notice: Subject to any disclaimer, the term of this patent is extended or adjusted under 35 U.S.C. 154(b) by 403 days.

(21) Appl. No.: 12/605,570

(22) Filed: Oct. 26, 2009

(65) Prior Publication Data

US 2010/0104612 A1 Apr. 29, 2010

(30) Foreign Application Priority Data

Oct. 27, 2008 (EP) .................................... 08167668

(51) Int. Cl.
*A61K 8/18* (2006.01)
*A61Q 15/00* (2006.01)
*A61K 8/02* (2006.01)
*A61K 8/92* (2006.01)
*A61K 8/11* (2006.01)
*A61K 8/33* (2006.01)
*A61K 8/37* (2006.01)
*A61K 8/58* (2006.01)
*A61K 8/65* (2006.01)
*A61K 8/73* (2006.01)

(52) U.S. Cl.
CPC .................. *A61K 8/92* (2013.01); *A61K 8/0229* (2013.01); *A61K 8/11* (2013.01); *A61K 8/33* (2013.01); *A61K 8/37* (2013.01); *A61K 8/585* (2013.01); *A61K 8/65* (2013.01); *A61K 8/73* (2013.01); *A61K 8/731* (2013.01); *A61K 2800/31* (2013.01); *A61K 2800/412* (2013.01); *A61K 2800/874* (2013.01)

(58) Field of Classification Search
None
See application file for complete search history.

(56) References Cited

U.S. PATENT DOCUMENTS

| | | | |
|---|---|---|---|
| 4,777,035 A | 10/1988 | Shin | |
| 5,043,161 A | 8/1991 | Scarpelli et al. | 424/401 |
| 5,126,061 A * | 6/1992 | Michael | 510/106 |
| 5,176,903 A | 1/1993 | Goldberg et al. | 424/66 |
| 5,508,259 A | 4/1996 | Holzner | |
| 6,045,835 A | 4/2000 | Soper | |
| 6,083,492 A * | 7/2000 | Modi | 424/65 |
| 6,106,875 A | 8/2000 | Soper | |
| 6,171,581 B1 | 1/2001 | Joshi et al. | 424/65 |
| 6,261,543 B1 | 7/2001 | Fletcher et al. | |
| 7,332,154 B2 | 2/2008 | Lemoine | |
| 8,518,425 B2 | 8/2013 | Chan | |
| 2003/0232025 A1 | 12/2003 | Colwell | 424/65 |
| 2004/0048771 A1 | 3/2004 | McDermott | |
| 2005/0180935 A1 | 8/2005 | Lemoine | |
| 2007/0036738 A1 * | 2/2007 | Fletcher et al. | 424/65 |
| 2008/0187504 A1 | 8/2008 | Fan | |
| 2008/0234172 A1 | 9/2008 | McGee | |
| 2009/0047226 A1 | 2/2009 | Teckenbrock et al. | 424/59 |

FOREIGN PATENT DOCUMENTS

| | | | |
|---|---|---|---|
| EP | 0 201 134 | | 11/1986 |
| EP | 0 303 461 | * | 2/1989 |
| EP | 0303461 | * | 2/1989 |
| EP | 0307723 A1 | | 3/1989 |
| EP | 0 385 534 | | 9/1990 |
| EP | 0 480 520 | | 4/1992 |
| EP | 0 519 531 | | 12/1992 |
| EP | 0 519 531 | * | 12/1995 |
| EP | 1 072 259 | | 1/2001 |
| EP | 1027147 B1 | | 5/2002 |
| EP | 1 533 364 | | 5/2005 |
| EP | 1 797 946 | | 6/2007 |
| FR | 2 839 658 | | 11/2003 |
| JP | 6271441 A2 | | 9/1994 |
| JP | 2004513187 T2 | | 4/2004 |
| JP | 2005187468 B2 | | 7/2005 |
| JP | 2008521942 T2 | | 6/2008 |
| WO | 2005/087181 | | 9/2005 |
| WO | 2006/056096 | | 6/2006 |
| WO | WO 2006/056096 | * | 6/2006 |
| WO | WO2006/056096 | * | 6/2006 |
| WO | WO2006056096 | * | 6/2006 |
| WO | 2006/082536 | | 8/2006 |
| WO | 2007/124889 | | 11/2007 |
| WO | WO2007135636 | * | 11/2007 |
| WO | 2008/144079 | | 11/2008 |

OTHER PUBLICATIONS

European Search Report in European Application No. 08 16 7668, Mar. 13, 2009.
European Search Report in European Application No. 08 16 7667, Mar. 18, 2009.
European Search Report in European Application No. 08 16 7669, Mar. 18, 2009.
Abstract of FR 2 839 658—published Nov. 21, 2003.
Co-pending Application: Applicant: Chan et al., U.S. Appl. No. 12/605,555, filed Oct. 26, 2009.
Co-pending Application: Applicant: Chan et al., U.S. Appl. No. 12/605,598, filed Oct. 26, 2009.
Wang (Ed.), "Microencapsulation Technology of Fragrance and Flavor and Applications Thereof", China Textile, 2008, pp. 215 and 244 with English translation.

* cited by examiner

*Primary Examiner* — Bethany Barham
*Assistant Examiner* — Melissa Javier
(74) *Attorney, Agent, or Firm* — Karen E. Klumas

(57) ABSTRACT

Fragrance leaches rapidly from capsules having shells made from cross linked gelatin into volatile silicone oils. Unfortunately such oils are much favored for anhydrous antiperspirant compositions. The rate and extent of leaching can be ameliorated greatly or nearly halted by employing as carrier oil, an ester oil or an ether oil, even in the presence of a significant fraction of volatile silicone oil. Consequently, the capability of antiperspirant compositions to generate detectable fragrance over an extended period after application to the skin is improved by employing ester or ether oil as all or part of the carrier liquid in which the antiperspirant is suspended.

10 Claims, No Drawings

ANTIPERSPIRANT COMPOSITIONS

The present invention relates to antiperspirant compositions and more particularly to anhydrous antiperspirant compositions delivering delayed-release fragrance.

Antiperspirant compositions comprising encapsulated fragrance are known in the art. Most of these compositions comprise moisture-sensitive encapsulates, such as those based on gum arabic or gum acacia, starch or certain modified starches, rather than the water-insoluble, shear-sensitive encapsulates employed in the present invention.

WO2006/056096 (Givaudan SA) discloses shear-sensitive encapsulates, largely focussing on their use in fabric conditioner compositions. Amongst the fabric conditioner examples, there is also disclosed as Example 9 an anhydrous antiperspirant composition, comprising gelatin capsules containing 20% fragrance. This prior art is silent concerning antiperspirant compositions comprising capsules having higher levels of encapsulated fragrance and lower levels of encapsulating shell.

One class of materials that has been proposed for encapsulating fragrances is water-insoluble and is shear-sensitive, which can also be described as friction-sensitive or pressure-sensitive. The fragrance is released by the encapsulates being rubbed, or abraded, possibly quite vigorously. This class of encapsulating materials has previously been contemplated primarily for use in household care compositions and especially fabric softener compositions that are aqueous and diluted by introduction into a rinse water, thereby taking advantage of the strength of the encapsulate shell made from such materials in aqueous conditions.

It has been found during the course of research leading to the instant invention that powdery shear sensitive encapsulates of a fragrance can be incorporated into anhydrous antiperspirant compositions in which a hydrophobic carrier liquid, which herein can alternatively be described as water-immiscible, and is commonly called an oil, suspends the particulate antiperspirant active material, optionally being gelled or thickened by a gellant or thickener. However, it has also been found that since the organic encapsulating material of such encapsulates is itself water-insoluble and the carrier liquid in which the fragrance capsules are suspended is water-immiscible, the two materials are so compatible that there is a significant risk of leaching of the fragrance out of the capsules during storage of the composition prior to its use by the consumer.

Premature leaching is potentially serious for several reasons. First, the loss of fragrance from the capsules during storage means that there is inherently less fragrance retained for release at the desired time by frictional contact. Thus, during time, the delayed release benefit of incorporating an encapsulated fragrance diminishes. An antiperspirant product is typically used, i.e. stored, over an extended period of time, measured in weeks or months rather than days, and it is desirable for the product to exhibit similar fragrance intensity over its period of use. Also, an antiperspirant product can be several weeks or even months old before it is purchased by the consumer, and may also be bought by the consumer a significant period of time before use begins. Secondly, individual perfume components can leach out of the encapsulate at different rates during storage, thereby changing the detectable odour with time. Manifestly, it is desirable for a fragrance to smell the same to the user over a normal period of use. Thirdly, an encapsulated fragrance can advantageously be used together with a non-encapsulated fragrance so as to combine an instant burst of fragrance when the antiperspirant is first applied with delayed, triggered release of fragrance subsequently. When fragrance has been prematurely released from the encapsulate during storage, it not only alters the balance between the fragrances, but is likely also to alter the actual characteristics of the non-encapsulated fragrance.

It is an object of the instant invention to ameliorate the loss of fragrance from water-insoluble friction-sensitive encapsulated fragrances during storage when the encapsulated fragrances are incorporated within anhydrous antiperspirant compositions comprising water-immiscible oil.

According to a first aspect of the present invention, there is provided an anhydrous antiperspirant composition comprising
particulate antiperspirant active,
water-insoluble, dry particulate friction-sensitive capsules of perfume, and
a liquid carrier for the particulate antiperspirant active and capsules of
perfume comprising at least one water-immiscible oil
wherein the water-immiscible oil comprises a water-immiscible ether oil and/or a water-immiscible ester oil or a blend thereof.

By the selection of such water-immiscible oils as the carrier oils for the friction-sensitive capsules of perfume fragrance alternatively referred to herein as perfume, it is possible to reduce significantly the rate and extent of leaching of fragrance components into the oil.

By the employment of such water-insoluble dry particulate capsules of perfume, it is possible to deposit on skin a residual fraction of shear-sensitive capsules of perfume particles that can be ruptured by normal arm movements in everyday living resulting in the passage of a garment across the surface of the skin or by the movement of skin around one part of the body relative to another, such as in the underarm, at a time when sweating is or is not occurring or irrespective of whether sweating has occurred. Advantage is accordingly taken of the sensitivity of such a dry particle on the skin surface to be ruptured by relative movements of garment or skin to skin. This enables improved masking of malodour and enhanced perception of fragrance over a prolonged period.

Although it is possible for some capsules having characteristics outside the preferred ranges identified herein to offer some residual fragrance release activity as contemplated herein, the selection of capsules satisfying those ranges combines manufacturing capability under the conditions for making anhydrous antiperspirant compositions with greater availability of releasable fragrance in the underarm.

According to a second aspect of the present invention, there is provided the use of a composition according to the first aspect simultaneously to prevent or reduce localised sweating by topical application of a composition according to the first aspect and to prolong perception of a perfume, possibly, even when sweating is not occurring or irrespective of whether sweating has occurred.

By employment of a composition according to the instant invention, perfume can be released for an extended period of time even in the absence of sweating that can act as a trigger to release perfume from some prior disclosed perfume-containing materials.

The instant invention relates to the selection of water-immiscible oils together with shear-sensitive fragrance capsules in anhydrous compositions. Such compositions can be applied from applicators, sometimes alternatively called dispensers that are either contact applicators or non-contact applicators. Alternatively, if in the shape of a bar can be applied like a soap bar, or, if in the form of a cream or liquid stored in a jar, is applied using fingers or a dedicated applicator such as a brush, or absorbed into or adsorbed onto a woven or non-woven applicator sheet.

A film of composition is dispensed from contact applicators by being transferred directly onto skin from the proximate applicator, whereas non-contact applicators are positioned at a significant distance away from the skin, such as from 10 to 20 cms, and a spray of composition directed towards the skin.

The term "shear sensitive" or "friction sensitive" or "pressure-sensitive" herein in relation to fragrance capsules, which herein is synonymous with microcapsules, indicates that the capsule is capable of releasing its perfume contents by rubbing an upper arm across the proximate chest wall or by impact of the upper arm on the proximate chest wall, contact being made by skin on skin or by skin on clothing worn on the arm and/or chest.

The encapsulating material used to form the shells of the shear-sensitive capsules herein is water-insoluble. This means that the perfume capsules are not ruptured merely by being in the presence of water, i.e., they are not water-sensitive. Water- or moisture-sensitive perfume capsules have previously been used in underarm products, release of perfume happening when the underarm becomes wet as a result of sweating. The present invention does not require the underarm to become wet for release of perfume from the capsules. This is particularly useful in antiperspirant compositions, as such compositions are designed to avoid sweat production in the underarms.

The encapsulating material used to form the shells of the shear-sensitive capsules herein is particularly suitably a cross-linked gelatin. One encapsulation process suitable for forming shear sensitive capsules is often called complex coacervation, which has been described, for example, in U.S. Pat. No. 6,045,835 and which process description is herein incorporated. In such a process, an aqueous solution of a cationic polymer, commonly gelatin or a closely related cationic polymer, is formed at an elevated temperature that is high enough to dissolve the gelatin, commonly at least 40° C. and in many instances it is unnecessary to exceed 70° C. A range of 40 to 60° C. is very convenient. Either before or after dissolution of the gelatin, an oil-in-water emulsion is formed by the introduction of a perfume oil. A polyanion or like negatively charged polymer, including in particular gum arabic or a carboxymethyl cellulose is introduced and the composition diluted until a pH of below pH5 and particular from pH4 to pH 4.5 is attained, whereupon a complex coacervate forms around the dispersed perfume oil droplets. The resultant shell is subsequently cross linked, with a short chain aliphatic di-aldehyde, for example $C_4$ to $C_6$, including in particular glutaraldehyde. The cross linking step is commonly conducted at a temperature of below ambient such as from 5 to 15° C., and particularly in the region of 10° C.

A second encapsulation method that is suitable for forming encapsulated perfumes comprises variations of the above process contemplated in WO2006/056096. In such variations, microcapsules comprising a blank hydrogel shell are first formed in a dry state and brought into contact with an aqueous or aqueous/alcoholic mixture of a fragrance compound, commonly diluted with a diluent oil. The fragrance compound is transported through the hydrogel shell by aqueous diffusion and is retained inside. The resultant fragrance-containing microcapsules are then dried to a powder, which for practical purposes is anhydrous. Although selection of the ratio of fragrance oil to diluent oil is at the discretion of the producer, and may be varied over a wide range, the ratio is often selected in the range of from 1:2 to 1:1, and particularly 3:4 to 1:1, fragrance:diluent oils.

The processes outlined herein are well suited to producing capsules having a volume average particle size in the range of from 30 to 100 μm, particularly up to 75 μm and especially 40 to 60 μm.

The proportion of shell material to core perfume oil is at the discretion of the producer, and is attainable by appropriately varying the proportions of the ingredients in the emulsion. It is desirable for the shell material to constitute from 10 to 80% of the capsules, particularly from 10 to 40% and especially from 12 to 25% by weight of the capsules. By varying the proportions of shell and core, the physical strength of the shell can be varied (for capsules of the same volume average particle size). Accordingly, capsules having the desired combination of characteristics can be selected.

In some preferred embodiments of the present invention, the fragrance oil constitutes from 70 to 85% by weight of the encapsulates and in such embodiments, the balance is provided by the shell.

In other preferred embodiments, the fragrance oil is present together with an oil diluent, for example providing from 25 to 75% by weight of the oil mixture held within the shell, and especially from 40 to 60% by weight. Desirably in such embodiments, the shell constitutes from 12 to 25% by weight of the encapsulates. In certain of such preferred embodiments, the fragrance constitutes from 35 to 50% by weight of the encapsulates, and is complemented by 35 to 50% by weight of diluent oil. If desired, in yet other embodiments, the composition contains some of the encapsulates that contain diluent oil and others that do not, the weight ratio of the two sets of encapsulates being selected in the range of from 25:1 to 1:25 at the discretion of the producer.

It is preferred for the volume average particle size of the capsules of the present invention to be at least 40 μm and in many desirable embodiments is up to 60 μm in diameter. Herein, unless otherwise indicated, the particle diameter of the capsules (D[4,3]) is that measured using a Malvern Mastersizer, the capsules being dispersed in cyclopentasiloxane (DC245) using a dispersion module mixer speed of 2100 rpm. Calculations were made using the General Purpose model, assuming a spherical particle shape and at Normal calculation sensitivity.

The capsules in the instant invention desirably have an average shell thickness in the range of from 0.25 to 10 μm and a ratio to the average particle diameter in the range of from 1:7 to 1:100. In some preferred embodiments, at least 95% by volume of the capsules have shell thickness of up to 2.5 μm, and commonly in the same or other preferred embodiments at least 95% by volume of the capsules have a shell thickness of at least 0.25 μm, such thicknesses herein desirably being measured as described herein. In some particularly preferred capsules, their average shell thickness lies in the range of from 0.4 to 1.5 μm, and/or the ratio of average capsule diameter to average thickness is at least 10:1 and often at least 30:1 or 40:1, to 80:1.

Calculations are suitably made using the General Purpose model, assuming a spherical particle shape and at Normal calculation sensitivity. The shell thickness can be measured by solidifying a dispersion of the capsules in a translucent oil, cutting a thin slice of the solid mass and using a scanning electron microscope to obtain an image of cut-through individual capsules, thereby revealing the inner and outer outline of its annular shell and hence its thickness.

It is desirable for the capsules to exhibit a Hysitron hardness in the range of from 0.5 MPa to 50 MPa and preferred capsules exhibit such a hardness in the range of from 5 to 25 MPa. It is also desirable for the capsules to have an "Apparent Reduced Elastic Modulus" in the range of from 20 to 30 MPa. The measurement of such parameters is described hereinafter for exemplified encapsulates.

The shear sensitive encapsulate or mixture of encapsulates can be employed in the antiperspirant compositions in an amount at the discretion of the manufacturer. Commonly, the amount is at least 0.05%, in many instances at least 0.1% and often at least 0.3% by weight of the composition. Usually, the amount is up to 5%, desirably up to 4% and in many instances is up to 3% by weight of the composition. A convenient range is from 0.5 to 2.5% by weight of the composition. Accordingly, the base compositions before introduction of propellant contain a proportionately higher proportion of the encapsulate.

The perfume oil employable herein can be selected as is conventional to attain the desired aesthetic result, and comprises usually a blend of at least 5 components, and often at least 20 components. The components can be synthetic or natural extractions, and in the case of natural oils or oils produced to mimic natural oils, are often mixtures of individual perfume compounds. The perfume oil can comprise, inter alia, any compound or mixture of any two or more such compounds coded as an odour (2) in the Compilation of Odor and Taste Threshold Values Data edited by F A Fazzalari and published by the American Society for Testing and Materials in 1978.

Often, though not exclusively, the perfume compounds acting as perfume components or ingredients in blends have a ClogP (octanol/water partition coefficient) of at least 0.5 and many a ClogP of at least 1. Many of the perfume components that are employable herein can comprise organic compounds having an odour that is discernible by humans that are selected within the chemical classes of aldehydes, ketones, alcohols, esters, terpenes, nitriles and pyrazines. Mixtures of compounds within classes or from more than one class can be blended together to achieve the desired fragrance effect, employing the skill and expertise of the perfumer. As is well known, within the same class, those compounds having a lower molecular weight, often up to about 200, tend to have a lower boiling point and be classified as "top notes", whereas those having a higher molecular weight tend to have a higher boiling point and be classified as middle or base notes. The distinction, though, is to some extent an arbitrary simplification, because the fragrance oils form a continuum and their characteristics are not significantly different close to on either side of an arbitrary boundary such as a boiling point of 250° C. or 275° C. Herein, the perfume can comprise any blend of oils boiling at below 250° C. (such as in the range 1 to 99% or 4 to 96%, 10 to 90% or 25 to 60%) with the balance provided by compounds having a boiling point above 250° C. The perfumer recognises that the lower boiling point compounds tend to evaporate more quickly after exposure, whereas higher boiling point compounds tend to evaporate more slowly, so that the desired aesthetic effect can be achieved by selecting the proportions of the faster and slower compounds—the faster providing an instant "hit" whilst the slower providing a longer lasting impact. It will also be recognised that a term such as high impact has also been used to describe low boiling point perfume compounds. The properties of the compound stay the same irrespective of whether they are called high impact or top note ingredients.

A further characteristic of a perfume compound is its odour detection threshold (ODT). Some perfume oils are much more easily detected by the human nose than others, but it is a very subjective measurement and varies considerably depending on the way that testing is performed, the prevailing conditions and the make-up of the panel, e.g. age, gender and ethnicity. As a qualitative means of differentiating between the aesthetic attributes of compounds, and enabling the perfumer to choose ingredients that are detected relatively easily, the ODT represents a useful guide, but quantitatively is more dubious.

Some of such perfume raw materials have a boiling point of less than, or equal to, 250° C., including some which are generally known to have a low odour detection threshold. Others within said list of perfume raw materials have a boiling point of greater than 250° C. of which some are also generally known to have a low odour detection threshold.

Alternatively or additionally, the fragrance incorporated into the capsules can comprise one or a mixture of perfume essential oils, either mixed with each or and/or with synthetic analogues and/or one or more individual perfume compounds, possibly extracted from blossom, leaves, seeds fruit or other plant material. Oils which are herein contemplated include oils from:—

Bergamot, cedar atlas, cedar wood, clove, geranium, guaiacwood, jasmin, lavender, lemongrass, lily of the valley, lime, neroli, musk, orange blossom, patchouli, peach blossom, petotgrain, pimento, rose, rosemary and thyme.

If desired, the composition can include one or more perfume ingredients that provide an additional function beyond smelling attractively. This additional function can comprise deodorancy. Various essential oils and perfume ingredients, for example those passing a deodorant value test as described in U.S. Pat. No. 4,278,658 provide deodorancy as well as malodour masking.

For many years, antiperspirant compositions have delivered the antiperspirant active from a composition also comprising volatile silicone oil, such oils having excellent sensory benefits. However, the present inventors have found that such oils encourage the leaching of perfume oils from the water-insoluble, shear sensitive capsules. Accordingly, in compositions according to the invention comprising volatile silicone oil, it is particularly important that the liquid carrier in which the capsules (and the antiperspirant active) are present comprises a water-immiscible ester oil and/or a water-immiscible ether oil or a blend thereof.

Herein, the liquid carrier and the water-immiscible oil comprised therein is deemed to exclude any fragrance oil.

The liquid carrier typically comprises nothing other than the water-immiscible oil.

The liquid carrier and the water immiscible oil are typically liquid at 20° C. "Water immiscible" should be understood to mean separating from water when mixed therewith at 20° C., in the absence of any emulsifying species.

The water immiscible oil is preferably a blend of more than one oil. For example, the water immiscible oil preferably comprises a volatile silicone as well as a water-immiscible ester oil and/or a water-immiscible ether oil or a blend thereof.

The ester oils can be aliphatic or aromatic. Suitable aliphatic ester oils comprise at least one residue containing from 10 to 26 carbon atoms and a second residue of at least 3 carbon atoms up to 26 carbon atoms. The esters may be mono or diesters, and in the latter be derived from a C3 to C8 diol or di carboxylic acid. Examples of such oils include isopropyl myristate, isopropyl palmitate and myristyl myristate.

It is especially desirable to employ an aromatic ester, including especially benzoate esters. Preferred benzoate esters satisfy the formula Ph-CO—O—R in which R is:— an aliphatic group containing at least 8 carbons, and particularly from 10 to 20 carbons such as from 12 to 15, including a mixture thereof, or an aromatic group of formula -A-Y-Ph in which A represents a linear or branched alkylene group containing from 1 to 4 carbons and Y represents an optional oxygen atom or carboxyl group. Particularly preferably, the aromatic ester comprises $C_{12-15}$ alkyl benzoate.

The ether oil preferably comprises a short chain alkyl ether of a polypropylene glycol (PPG), the alkyl group comprising from C2 to C6, and especially C4 and the PPG moiety comprising from 10 to 20 and particularly 14 to 18 propylene glycol units. An especially preferred ether oil bears the INCI name PPG14-butyl ether.

The ester and ether oils herein are selected having a boiling point in excess of 100° C. This enables them to be employed with all wax systems for solidifying the carrier oil that typically melt at no higher than 95° C., and commonly between 65 and 85° C. For sticks made using small molecule gelling agents, it is preferable to select oils having a boiling point in excess of 150° C., and they, naturally, are suitable in conjunction with wax systems too.

The carrier oil need not consist entirely of either ester or ether oil or a mixture of the ester oil and ether oil. The ester and ether oils can be present in the composition in a weight ratio to each other of from 1:0 to 0:1, and in some embodiments from 10:1 to 1:10. Indeed, though such oils have a number of other beneficial properties, such as for example, reducing the extent to which the antiperspirant formulation is visible after application on the skin, compositions in which the oil blend contains only a minor as compared with a major proportion of such ether and ester oils tend to exhibit sensory attributes preferred by many consumers. In practice, it is desirable for greater than 5% by weight of the oil blend, especially greater than 10% and especially greater than 15% by weight of the oil blend to be furnished by the ester and ether oils. The combined weight of the two oils is preferably less than 60%, particularly less than 50% and especially less than 40% of the weight of the oil blend:

Although it has been found that fragrance oils leach comparatively quickly and to a comparatively large extent into volatile silicone oils alone, it has been found that when an ester oil and/or an ether oil is present in the oil blend, the reduction in the rate and extent of leaching approaches or even exceeds that which is obtained by the ether/ester oil alone. Accordingly, it is highly desirable for the oil blends employed in anhydrous antiperspirant compositions according to the present invention to include a fraction of volatile silicone oil, for example in a weight ratio to the combined weight of ester and ether oil of from 6.5:1 to 1:6.5, and in many embodiments from 6:1 to 1:1, taking into account not only the beneficial fragrance-leaching reduction caused by including the ester and ether oils but also the beneficial sensory effects achieved by incorporating a significant fraction of volatile silicone oils. In many desirable embodiments, the weight proportion of volatile silicone oil in the oil blend is greater than 5%, especially greater than 10% and particularly greater than 20%. Commonly, the weight proportion is less than 87.5%, in many instances less than 80% w/w and on occasions less than 65% w/w. In one embodiment the volatile silicone oil is from 30 to 70% by weight of the water immiscible oil.

Herein, a volatile silicone oil is a liquid polyorgano-siloxane having a measurable vapour pressure at 25° C. of at least 1 Pa, and typically in a range of from 1 or 10 Pa to 2 kPa. Volatile polyorganosiloxanes can be linear or cyclic or mixtures thereof. Preferred cyclic siloxanes, otherwise often referred to as cyclomethicones, include polydimethylsiloxanes and particularly those containing from 3 to 9 silicon atoms, preferably at least 4 and especially at least 5 silicon atoms. Preferred cyclomethicones contain not more than 7 silicon atoms and very preferably up to 6 silicon atoms. Volatile silicone oils herein desirably contain on weight average from 4.5 to 5.9 silicone atoms, and especially at least 4.9.

Preferred linear polyorganosiloxanes include polydimethylsiloxanes containing from 3 to 9 silicon atoms. The volatile siloxanes normally by themselves exhibit viscosities of below $10^{-5}$ m$^2$/sec (10 centistokes), and particularly above $10^{-7}$ m$^2$/sec (0.1 centistokes), the linear siloxanes normally exhibiting a viscosity of below $5 \times 10^{-6}$ m$^2$/sec (5 centistokes). The volatile silicones can also comprise linear or cyclic siloxanes such as the aforementioned linear or cyclic siloxanes substituted by one or more pendant —O—Si(CH$_3$)$_3$ groups, the resultant compounds desirably containing not more than 7 silicon atoms. Examples of commercially available silicone oils include oils having grade designations 344, 345, 244, 245 and 246 from Dow Corning Corporation; Silicone 7207 and Silicone 7158 from Union Carbide Corporation; and SF1202 from General Electric.

The carrier oil blend can further comprise one or more other water-immiscible oils that have a melting point of below 20° C. and a boiling point of above 100° C. and preferably above 150° C., including hydrocarbon oils, including preferably non-volatile hydrocarbon oils, non-volatile silicone oils and aliphatic monohydric alcohols. Such non-volatile water-immiscible oils, sometimes referred to as emollient oils, can desirably be included to alter the sensory attributes of the compositions containing, such as to soften the skin or to assist in masking the visibility of particulate materials deposited on the skin. However, it is desirable to restrict the proportion of such non-volatile oils to less than 30% by weight of the oil blend, and in many compositions, according to the instant application, the total proportion of such oils is from 5 to 20% by weight.

Examples of suitable non-volatile hydrocarbon oils include polyisobutene and hydrogenated polydecene. Examples of suitable non-volatile silicone oils include dimethicones and linear alkylarylsiloxanes. The dimethicones typically have an intermediate chain length, such as from 20 to 100 silicon atoms. The alkylarylsiloxanes are particularly those containing from 2 to 4 silicon atoms and at least one phenyl substituent per silicon atom, or at least one diphenylene group. The aliphatic alcohol desirably is a branched chain monohydric alcohol containing from 12 to 40 carbon atoms, and often from 14 to 30 carbon atoms such as isostearyl alcohol.

One further class of ester oils that can constitute a fraction of the ester oils contemplated in the invention compositions comprises natural plant oils, commonly containing glyceride esters and in particular the glyceride triesters of unsaturated C18 aliphatic carboxylic acids, such as linoleic acid, linolenic acid or ricinoleic acid, including isomers such as linolenelaidic acid, trans 7-octadecenoic acid, parinaric acid, pinolenic acid punicic acid, petroselenic acid, columbinic acid and stearidonic acid. Examples of such beneficial natural oils include caster oil, coriander seed oil, impatiens balsimina seed oil, parinarium laurinarium kernel fat, sabastiana brasilinensis seed oil borage seed oil, evening primrose oil, aquilegia vulgaris oil, for and sunflower oil and safflower oil. Such oils can desirably comprise from 1 to 10% by weight of the oil blend.

The compositions of the invention also comprise an antiperspirant active. Antiperspirant actives are preferably incorporated in an amount of from 0.5-50%, particularly from 5 to 30% and especially from 10% to 26% of the weight of the composition. It is often considered that the main benefit from incorporating of up to 5% of an antiperspirant active in a stick composition is manifest in reducing body odour, and that as the proportion of antiperspirant active increases, so the efficacy of that composition at controlling perspiration increases.

Antiperspirant actives for use herein are often selected from astringent active salts, including in particular aluminium, zirconium and mixed aluminium/zirconium salts, including both inorganic salts, salts with organic anions and complexes. Preferred astringent salts include aluminium, zirconium and aluminium/zirconium halides and halohydrate salts, such as chlorohydrates.

Aluminium halohydrates are usually defined by the general formula $Al_2(OH)_xQ_y \cdot wH_2O$ in which Q represents chlorine, bromine or iodine, x is variable from 2 to 5 and x+y=6 while $wH_2O$ represents a variable amount of hydration. Especially effective aluminium halohydrate salts, known as activated aluminium chlorohydrates, are described in EP-A-6739 (Unilever N V et al), the contents of which specification is incorporated herein by reference. Such activated aluminium chlorohydrates are made by a method in which the weight concentration of aluminium compounds in the solution is controlled within specified limits and simultaneously the temperature of that solution is controlled within a specified elevated temperature range whilst polymeric aluminium species are formed, and drying conditions are strictly controlled as described in the said EP-A-6739. Some activated salts do not retain their enhanced activity in the presence of water but are useful in substantially anhydrous formulations, i.e. formulations that do not contain a distinct aqueous phase.

Zirconium actives can usually be represented by the empirical general formula: $ZrO(OH)_{2n-nz}B_z \cdot wH_2O$ in which z is a variable in the range of from 0.9 to 2.0 so that the value 2n-nz is zero or positive, n is the valency of B, and B is selected from the group consisting of chloride, other halide, sulphamate, sulphate and mixtures thereof. Possible hydration to a variable extent is represented by $wH_2O$. Preferable is that B represents chloride and the variable z lies in the range from 1.5 to 1.87. In practice, such zirconium salts are usually not employed by themselves, but as a component of a combined aluminium and zirconium-based antiperspirant.

The above aluminium and zirconium salts may have coordinated and/or bound water in various quantities and/or may be present as polymeric species, mixtures or complexes. In particular, zirconium hydroxy salts often represent a range of salts having various amounts of the hydroxy group. Zirconium aluminium chlorohydrate may be particularly preferred.

Antiperspirant complexes based on the above-mentioned astringent aluminium and/or zirconium salts can be employed. The complex often employs a compound with a carboxylate group, and advantageously this is an amino acid. Examples of suitable amino acids include dl-tryptophan, dl-β-phenylalanine, dl-valine, dl-methionine and β-alanine, and preferably glycine which has the formula $CH_2(NH_2)COOH$.

It is highly desirable to employ complexes of a combination of aluminium halohydrates and zirconium chlorohydrates together with amino acids such as glycine, which are disclosed in U.S. Pat. No. 3,792,068 (Luedders et al). Certain of those Al/Zr complexes are commonly called ZAG in the literature. ZAG actives generally contain aluminium, zirconium and chloride with an Al/Zr ratio in a range from 2 to 10, especially 2 to 6, an Al/Cl ratio from 2.1 to 0.9 and a variable amount of glycine. Actives of this preferred type are available from B K Giulini, from Summit and from Reheis, though with differing particle size distributions.

Many aluminium and/or zirconium-containing astringent antiperspirant salts employed herein have metal:chloride mole ratio in the range of 1.3:1 to 1.5:1. Others having a lower metal:chloride mole ratio, such as from 1:1 to 1.25:1 tend to generate lower pHs when applied to skin and thus tend to be more irritating.

The proportion of solid antiperspirant salt in a suspension composition normally includes the weight of any water of hydration and any complexing agent that may also be present in the solid active.

Many particulate antiperspirants employed in the instant invention have a refractive index (RI) of at least 1.49 and not higher than 1.57. Actives which are free from zirconium tend to have an RI of from 1.49 to 1.54, depending on their formula and at least partly on their residual water content. Likewise, actives which contain zirconium tend to have an RI of from 1.52 to 1.57.

The selection of the antiperspirant active material desirably takes into account the type of applicator from which it is dispensed. Thus, in many particularly preferred embodiments in which the composition is dispensed from a contact applicator, for example using a stick, cream (soft solid) or roll-on dispenser, the antiperspirant active comprises an aluminium-zirconium active, such as AZAG. However, in other highly preferred embodiments in which the composition is dispensed as a spray, such as using an aerosol dispenser, the antiperspirant active is highly desirably an aluminium chlorohydrate (ACH) or an activated aluminium chlorohydrate (AACH).

The antiperspirant active employed herein comprises small particles, their average particle size and distribution commonly being selected in accordance with the nature of the applicator from which the composition is dispensed.

For incorporation of compositions according to the present invention, desirably at least 90%, preferably at least 95% and especially at least 99% by weight of the particles having a diameter in the range of from 0.1 μm up to 100 μm. For incorporation in contact applicators, such as stick, soft solid or roll-on dispensers, the antiperspirant particles usually have an average particle diameter of at least 1 μm and especially below 20 μm. In some highly desirable contact compositions, the particles by weight have an average particle size of at least 2 μm and particularly below 10 μm, such as in the range of from 3 to 8 μm.

For incorporation in non-contact applicators and especially in aerosols in which the composition is expelled from the dispenser by a propellant gas, possibly augmented by a mechanical or electromechanical propulsive means, it is especially desirable for less than 5% by weight, particularly less than 1% by weight and advantageously none of the particles to have a diameter of below 10 μm. Preferably for inclusion in aerosol compositions, the particles have a diameter of below 75 μm. In many preferred aerosol compositions, the antiperspirant has an average ($D_{50}$) particle diameter in the range of from 15 to 25 μm. The particle size of the antiperspirant active or mixture of actives can be measured using a Malvern Mastersizer, similarly to measurement of the perfume microcapsules size, as mentioned hereinbefore.

One method of seeking to minimise visible whiteness employs antiperspirant active material that is free or substantially free from hollow particles. In this context, substantially free indicates a content of less than 10% by weight hollow spheres, and preferably less than 5% by weight. Some drying techniques, e.g. spray drying, can produce materials which contain greater than such a proportion of hollow spheres, the proportion can be reduced by milling the particulate material, such as by ball or swing milling.

The invention compositions can, if desired, include one or more thickeners or gellants (sometimes called structuring or solidifying agents) to increase the viscosity of or solidify the oil blend in which the particulate materials are suspended as is appropriate for application from respectively roll-on dispensers, soft solid (anhydrous cream) dispensers or stick dispensers. Such thickeners or gellants are selected by the skilled man and enough of them is incorporated to attain the desired viscosity or hardness of the resulting roll-on, lotion or soft solid composition, the actual amount employed taking into account the inherent thickening or gelling capability of the chosen material or combination of materials and their ability to form such a physical form.

In alternative embodiments, for application from a pressurized aerosol dispenser, the anhydrous composition, deemed to be a base composition and desirably comprising a suspending aid, is blended with a propellant.

For application from a roll-on, sufficient thickener is introduced to increase the viscosity of the resultant composition to within the range, typically, of from 1000 to 7000 mPa·s and particularly within 2500 to 5500 mPa·s. Viscosities herein are measured in a Brookfield RVT viscometer equipped with a stirrer TA and Hellipath, rotating at 20 rpm at 25° C.

Herein, the thickener for a roll-on formulation can be selected from suspending agents that can be employed for suspending particulates in a base composition comprising the water-immiscible oil blend, such as particulate silica, especially fumed silica and particulate montmorillonite or bentonite clay, optionally surface treated with a hydrophobic organic compound. Suitable examples are available under the trade names respectively Cab-O-sil and Bentone. Yet other thickeners can comprise oil soluble petrolatum or waxes, such as the waxes described hereinbelow in respect of soft solid or/and sticks. Waxes typically are considered to melt at above 40° C. and particularly between 55 and 95° C. Such waxes can include ester waxes, including C12 to C24 linear fatty alcohols, waxes obtained from animals or plants, often after hydrogenation, silicone elastomers and silicone waxes. The thickener system can comprise a mixture of particulate thickeners, a mixture of waxes or a mixture of materials from both. The proportion of thickener or mixture of thickeners is often selected in the range of from 1:30 to 1:12.5 parts per part by weight of oil blend. The viscosity can also be increased by selecting as part of the carrier oil blend, for example from 10 to 20% w/w, relatively viscous non-volatile dimethicone oils or/and hydrogenated polydecene.

For use as a soft solid, sufficient thickener is introduced to increase the viscosity of the resultant composition to a hardness of from 0.003 to 0.5 Newton/mm$^2$, and commonly from 0.003 or 0.01 up to 0.1 Newton/mm$^2$. Hardness can be measured using a Stable Micro Systems TA.XT21 Texture Analyser. A metal sphere, of diameter 9.5 mm, is attached to the underside of its 5 kg load cell, and positioned just above the sample surface. Under control of Expert Exceed™ software, the sphere is indented into the sample at an indentation speed of 0.05 mm/s for a distance of 7 mm and reversed to withdraw the sphere from the sample at the same speed. Data comprising time(s), distance (mm) and force (N) is acquired at a rate of 25 Hz. The hardness H at a penetration of 4.76 mm is calculated using the formula $$H=F/A$$

in which H expressed in N·mm$^{-2}$, F is the load at the same traveled distance in N and A is the projected area of the indentation in mm$^{-2}$.

In certain embodiments of the present invention, the water-immiscible oil is solidified, giving compositions termed "stick compositions" herein. Such compositions preferably comprise both a water immiscible ester oil and a water immiscible ether oil, as described herein, especially when a volatile silicone oil is also present.

Stick compositions herein desirably have a hardness as measured in a conventional penetration test of less than 30 mm, preferably less than 20 mm and particularly desirably less than 15 mm. Many have a penetration of from 7.5 to 12.5 mm. The conventional penetration test employed herein, utilises a lab plant PNT penetrometer equipped with a Seta wax needle (weight 2.5 grams) which has a cone angle at the point of the needle specified to be 9°10'+/−15'. A sample of the composition with a flat upper surface is used. The needle is lowered onto the surface of the composition and then a penetration hardness measurement is conducted by allowing the needle with its holder to drop under the combined weight of needle and holder of 50 grams for a period of five seconds after which the depth of penetration is noted. Desirably the test is carried out at six points on each sample and the results are averaged.

The gellants for forming stick compositions herein are usually selected from one or more of two classes, viz-fibre-forming non-polymeric small-molecule gelling agents (viz SMGAs), and waxes, optionally supplemented if desired by incorporation of a particulate silica and/or an oil-soluble polymeric thickener. The waxes described above not only are thickeners for liquid or cream compositions but also are suitable to act as gellants for solids and soft solids.

The term "wax" is conventionally applied to a variety of materials and mixtures which have similar physical properties, namely that:—
  they are solid at 30° C. and preferably also at 40° C.;
  they melt to a mobile liquid at a temperature above 40° C. and generally below 95° C. and preferably in a temperature range of 55° C. to 90° C.;
  they are water-insoluble and remain water-immiscible when heated above their melting point.

Waxes employed herein as gellants, or in other embodiments as thickeners, are often selected from hydrocarbons, linear fatty alcohols, silicone polymers, esters of fatty acids or mixtures containing such compounds along with a minority (less than 50% w/w and often less than 20% w/w) of other compounds. Naturally occurring waxes are often mixtures of compounds which include a substantial proportion of fatty esters.

Waxes usually form crystals in the water-immiscible liquid when it cools from the heated state during processing, often taking the form of needles or platelets depending on the specific wax.

Examples of hydrocarbon waxes include paraffin wax, ozakerite, microcrystalline wax and polyethylene wax, the last named desirably having an average molecular weight of from 300 to 600 and advantageously from 350 to 525.

Linear fatty alcohols commonly contain from 14 to 40 carbon atoms and often from 16 to 24. In practice, most contain an even number of carbon atoms and many comprise a mixture of compounds, even those that are nominally a single one such as stearyl alcohol. Other alcohols include behenyl alcohol Examples of ester waxes include esters of $C_{16}$-$C_{22}$ fatty acids with glycerol or ethylene glycol, which can be isolated from natural products or more conveniently synthesised from the respective aliphatic alcohol and carboxylic acid.

Examples of natural waxes include beeswax, woolwax and spermeceti wax of animal origin, and caster wax, jojoba wax, carnauba wax and candelilla wax which are of vegetable origin. The vegetable waxes are commonly obtained by hydrogenation of the corresponding plant oil, containing triglyceride esters of unsaturated fatty acids. Mineral waxes can be extracted from fossil remains other than petroleum. Montan wax, which is an example of mineral wax, includes non-glyceride esters of carboxylic acids, hydrocarbons and other constituents.

Further waxes employable herein comprise silicone polymer waxes, including waxes which satisfy the empirical formula:—

$$R—(SiMe_2-O—)_x—SiMe_2R$$

in which x is at least 10, preferably 10 to 50 and R represents an alkyl group containing at least 20 carbons, preferably 25 to 40 carbons, and particularly having an average linear chain length of at least 30 carbons.

Other silicone waxes comprise copolymers of dimethicone and alkyloxymethicone, satisfying the general formula:—

$$Y—(SiMe_2-O—)_y(Si[OR']Me-O—)_z—Y'$$

in which Y represents $SiMe_2$-O, Y' $SiMe_2$, R' an alkyl of at least 15 carbons preferably 18 to 22 such as stearyl, y and z are both integers, totaling preferably from 10 to 50.

Some preferred combinations of waxes include stearyl alcohol with an ester wax such as cater wax, often in a weight ratio of from 10:1 to 3:1.

Waxes useful in the present invention will generally be those found to thicken water-immiscible oils such as cyclomethicones when dissolved therein (by heating and cooling) at a concentration of 5 to 15% by weight.

The second class of thickeners or gellants for sticks for soft solids comprises fibre-forming SMGAs. Such gellants are dissolved in a water-immiscible blend of oils at elevated temperature and on cooling precipitate out to form a network of very thin strands that are typically no more than a few molecules wide. One particularly effective category of such thickeners comprises N-acyl amino acid amides and in particular linear and branched N-acyl glutamic acid dialkylamides, such as in particular N-lauroyl glutamic acid di n-butylamide and N-ethylhexanoyl glutamic acid di n-butylamide and especially mixtures thereof. Such amido gellants can be employed in anhydrous compositions according to the present invention, if desired, with 12-hydroxystearic acid.

Other amido SMGAs include 12-hydroxystearic acid amides, and amide derivatives of di and tribasic carboxylic acids as set forth in WO 98/27954, including notably alkyl N,N'dialkyl succinamides.

Further suitable amido-containing SMGAs are described in U.S. Pat. No. 6,410,003 and other suitable SMGAs are disclosed in U.S. Pat. No. 7,332,153, U.S. Pat. No. 6,410,001, U.S. Pat. No. 6,321,841, and U.S. Pat. No. 6,248,312.

Naturally, a combination of two or more gellants can be employed, such as a wax or mixture of waxes alone, or a mixture of SMGAs alone of a mixture of a wax or waxes plus an SMGA or SMGAs, such as are described hereinabove.

The gellant is often employed in the stick or soft solid composition at a concentration of from 1.5 to 30%, depending on the nature of the gellant or gellants, the constitution of the oil blend and the extent of hardness desired. When an SMGA is employed as the principal gellant, its concentration is typically in the range of from 1.5 to 7.5% w/w for amido gellants or mixtures of them and for 5 to 15% for ester or sterol gellants. When a wax is employed as the principal gellant, its concentration is usually selected in the range of from 10 to 30% w/w, and particularly from 12 to 24% w/w. In many compositions, this corresponds to a weight ratio of the oil ba to the carrier oils selected in the range of 1:30 to 1:2.

If a wax is used which forms a network of fibres, the amount of it may be from 0.5 to 7% by weight of the composition. If a wax is used which does not form such a network, for instance a wax which crystallizes as spherulitic needles or as small platelets, the amount may well be from 2% or 3% up to 10%, 12% or 15% of the composition. Silicone waxes are an example of waxes which crystallize as small platelets.

Some highly desirable compositions comprise in combination a first gellant with a second gellant. The total amount of second gellant may range from 0.5% or 1% of the composition up to 9%, 10% or 15%.

In general, soft solid compositions herein can include one or more of the gellants employed to make a firm stick as described above, but employing a lower concentration of the respective gellant. Thus, the concentration of such gellants is often selected in the range of from 0.5 to 15% w/w of the composition and in many instances from 1 to 10% w/w.

However, it can be especially desirable to employ an oil-soluble polymer as thickening agent for forming a soft solid, for example selected in the range of from 2 to 20% w/w of the composition. Likewise such polymers can be included in stick compositions.

One category of oil-soluble polymer which has been found suitable is a polysaccharide esterified with monocarboxylic acid containing at least 12 carbon atoms, and preferably a dextrin fatty acid ester such as dextrin palmitate or dextrin stearate. Commercial products are available under the trade mark Rheopearl.

A second category of polymer thickener comprises polyamides for example those discussed in U.S. Pat. No. 5,500,209 or U.S. Pat. No. 6,353,076.

A third category of thickening comprises block copolymers of styrene with ethylene propylene and/or butylene available under the trade name KRATON, and particularly styrene ethylene/butylene styrene linear block copolymers. A related category of thickening polymer comprises polymers of alpha methylstyrene and styrene, such as those under the trade name KRISTALEX, eg KRISTALEX F85 having a mean molecular weight of approximately 1200. Yet another thickening polymer comprises alkyl substituted galactomannan available under the trade name N-HANCE AG.

A still further class of thickening polymers co-polymers of vinyl pyrrolidone with polyethylene containing at least 25 methylene units, such as triacontanyl polyvinylpyrrolidone, under the trade name Antaron WP-660.

Such thickening polymer is often employed in a weight ratio to the oil blend that is selected in the range of from 1:30 to 1:5, taking into account the hardness of the soft solid that is desired, the inherent ability of the chosen polymer to increase viscosity and the presence or otherwise of an additional thickener.

A further class of material which is well suited to forming or contributing to the formation of soft solid compositions comprises silicone elastomers. Such materials are conventionally formed by the hydrosilation of vinyl silicone fluids by hydrosiloxane or MQ hydride fluids. Commonly, for anhydrous compositions, the elastomer is non-emulsifying and especially is a dimethicone/vinyldimethicone cross polymer. Such materials are capable of absorbing a substantial proportion of hydrophobic oils, including cyclomethicones, and are commonly supplied as a dispersion of the active material in cyclomethicone fluid or a non-volatile oil, typically at a concentration in the region of 10 to 20% by weight. Such elastomers are desirably present at a concentration of from 1 to 10% by weight of the composition.

A thickener especially well suited to forming or contributing to the formation of a soft solid composition comprises a particulate silica and especially a fumed silica.

It is desirable to include at least 2% and especially at least 2.5% by weight of the silica in the composition, such as in the range of up to 10% by weight.

The anhydrous compositions can contain one or more optional ingredients, such as one or more of those selected from those identified below.

Optional ingredients include wash-off agents, often present in an amount of up to 10% w/w to assist in the removal of the formulation from skin or clothing. Such wash-off agents are typically nonionic surfactants such as esters or ethers containing a $C_8$ to $C_{22}$ alkyl moiety and a hydrophilic moiety which can comprise a polyoxyalkylene group (POE or POP) and/or a polyol.

The compositions herein can incorporate one or more cosmetic adjuncts conventionally contemplatable for cosmetic solids or soft solids. Such cosmetic adjuncts can include skin feel improvers, such as talc or finely divided high molecular weight polyethylene, (i.e. not a wax) for example Accumist, in an amount of 1 up to about 10%; a moisturiser, such as glycerol or polyethylene glycol (mol wt 200 to 600), for example in an amount of up to about 5%; skin benefit agents such as allantoin or lipids, for example in an amount of up to 5%; colours; skin cooling agents other than the already mentioned alcohols, such as menthol and menthol derivatives, often in an amount of up to 2%, all of these percentages being by weight of the composition. A further optional ingredient comprises a preservative, such as ethyl or methyl paraben or BHT (butyl hydroxy toluene) such as in an amount of from 0.01 to 0.1% w/w.

Aerosol base compositions desirably additionally comprise a suspending aid, sometimes called a bulking agent which is typically a powdered silica or a layered clay, such as a hectorite, bentonite or montmorillonite. The layered clay is optionally hydrophobically surface treated. Particularly suitable surface treated clays are available under the trade mark Bentone, such as Bentone 38. The suspending aid often constitutes from 0.5 to 6% by weight, particularly 1.5 to 5.5% by weight, of the base aerosol composition. Aerosol base compositions desirably also can contain a swelling aid to assist swelling of the layered clay, often selected in a proportion of from 0.005 to 0.5% by weight of the aerosol base composition and particularly in a weight ratio to the clay of from 1:10 to 1:75. Suitable swelling aids include especially propylene carbonate and triethyl citrate.

The invention compositions herein can additionally contain a water-soluble polymer comprising a Bronsted acid group that cooperates synergistically with the aluminium or aluminium/zirconium antiperspirant active to enhance antiperspirant efficacy. Such a material is referred to in U.S. Pat. No. 6,616,921 as a co-gellant (because it assists the antiperspirant active to gel in eccrine pores) and is described therein. Preferred examples of such a co-gellant are polymers having a molecular weight of at least 50,000 derived at least in part from maleic acid or maleic anhydride, such as Gantraz™ AN119, AN139 or AN169. The co-gellant is often selected in a weight ratio to the aluminium or aluminium/zirconium salt of from 1:15 to 1:2.

The compositions herein can optionally comprise one or more non-encapsulated fragrances, for example in a weight % of from 0.01 to 4% of the composition, and particularly from 0.1 to 1.5%. The non-encapsulate fragrance is desirably incorporated into the composition in a weight ratio to the shear-sensitive encapsulate in the range of from 5:1 to 1:5. The non-encapsulated fragrance can be created from the same palette of perfume materials described above. The non-encapsulated fragrance can, if desired, be the same as or similar to the encapsulated fragrance, but it is often more attractive if the two fragrances are different, because this minimises the extent to which the nose has become desensitised to perfume. Choice of the various fragrances and the differences between them, such as proportion of top notes, is primarily a matter of aesthetic judgement.

Additionally or alternatively to the non-encapsulated fragrance, if desired the compositions herein can comprise fragrance encapsulated in a water-sensitive shell, such that when a person sweats, the aqueous excretion ruptures the shell releasing fragrance. Such water-sensitive encapsulates are described for example in EP0303461. Additionally or likewise alternatively, the compositions herein can comprise a cyclic oligosaccharide such as cyclodextrins, including a or β cyclodextrin, each optionally substituted by a methyl or hydroxy-propyl group that associates reversibly with free fragrance. Such materials are described in EP1289484. The composition can contain the water-sensitive fragrance encapsulate and/or cyclic oligosaccharide in an amount of from 0.1% to 4% by weight of the composition.

The weight ratio of shear-sensitive encapsulate to water-sensitive encapsulate and/or cyclic oligosaccharide is often selected in the range of from 5:1 to 1:5.

The invention compositions, be they the full composition for use in contact applicators or the base composition for mixture with a propellant for aerosol compositions desirably are substantially or totally free from water-soluble short chain monohydric alcohols (commonly recognised as up to $C_6$) and especially ethanol. Substantially in this context indicates a proportion of less than 5% and preferably less than 1% by weight of the respective full or base composition.

Herein, unless the context demands otherwise, all weights, %s, and other numbers can be qualified by the term "about".

The invention compositions can be made by way of the methods herein described. However, it is especially desirable for the fragrance capsules to be incorporated into the composition with gentle mixing, at a rate and power input that does not damage the capsules, and, for the same reason, the composition is subsequently not subjected to shear or intensive mixing.

One convenient process sequence for preparing a stick or soft composition according to the present invention comprises first forming a solution of the structurant combination in the water-immiscible liquid or one of the water-immiscible liquids. This is normally carried out by agitating the mixture at a temperature sufficiently high that all the structurants dissolve (the dissolution temperature) such as a temperature in a range from 70 to 140° C. Any oil-soluble cosmetic adjunct can be introduced into oil phase, either before or after the introduction of the gellants. However, the fragrance oil, be it encapsulated or free, is commonly the last ingredient to be incorporated into the composition, after the antiperspirant active on account of its sensitivity often to elevated temperature. Commonly, the resultant structurant solution is allowed to cool to a temperature that is intermediate between that at which the gellants dissolved and the temperature at which it would set, often reaching a temperature in the region of 60 to 90° C.

In some routes, the carrier oils can be mixed together prior to introduction of the gellants and the antiperspirant or deodorant active. In other preparative routes, it is desirable to dissolve all or a fraction of the gellants and especially for amido gellants in a first fraction of the composition, such as a branched aliphatic alcohol, e.g. isostearyl alcohol or octyldodecanol, optionally in conjunction with an alcohol having some water-miscibility and boiling point above the dissolution temperature of the amido gellant in the alcoholic fluid. This enables the remainder of the carrier fluids to avoid being heated to the temperature at which the structurants dissolve or melt. Such a process commonly involves mixing the fractions intensively in for example a "Sonolator™". In the invention compositions, the fragrance capsules are most desirably introduced after any intensive mixing step. The proportion of the carrier fluids for dissolving the structurants is often from 25 to 50% by weight of the carrier fluids.

In said other preparative routes the particulate material is introduced into preferably a second fraction of the carrier oils, for example silicone and/or ester and/or hydrocarbon oils, and thereafter the first fraction containing dissolved structurant and second fraction containing suspended particulate material are mixed at a temperature above that at which the composition gels, and often from 5° C. to 30° C. above the regular setting temperature of the composition, dispensing containers are filled and cooled or allowed to cool to ambient temperature. Cooling may be brought about by nothing more than allowing the container and contents to cool. Cooling may be assisted by blowing ambient or even refrigerated air over the containers and their contents.

Suspension roll-on compositions herein can be made by first charging a mixing vessel equipped with agitation means such as a stirrer or a recycle loop with the oils simultaneously or sequentially, and thereafter charging the vessel with the antiperspirant/deodorant active ingredient, the thickener and any optional ingredient and heating the composition to the extent necessary to dissolve any organic thickener in the oil blend. Thereafter, the resultant fluid composition is discharged into roll-on dispensers through the open top and the ball (or more unusually cylindrical roller) inserted and the cap fitted.

Aerosol products herein comprise a base composition comprising an antiperspirant and/or deodorant active suspended in an oil blend together with the fragrance capsules, suspending agent and optional ingredients that is blended with a propellant, commonly in a weight ratio of blend to propellant of from 1:1 to 1:15, and in many formulations from 1:3 to 1:9. The propellant is commonly either a compressed gas or a material that boils at below ambient temperature, preferably at below 0° C., and especially at below −10° C. Examples of compressed gasses include nitrogen and carbon dioxide. Examples of low boiling point materials include dimethylether, $C_3$ to $C_6$ alkanes, including in particular propane, butanes and isobutane, optionally further containing a fraction of pentane or isopentane, or especially for use in the USA the propellant is selected from hydrofluorocarbons containing from 2 to 4 carbons, at least one hydrogen and 3 to 7 fluoro atoms.

Aerosol products can be made in a conventional manner by first preparing a base composition, charging the composition into the aerosol can, optionally introducing the fragrance into the can after the base composition, (late fill addition), fitting a valve assembly into the mouth of the can, thereby sealing the latter, and thereafter charging the propellant into the can to a desired pressure, and finally fitting an actuator on or over the valve assembly together with an overcap if the can does not employ through the cap spraying.

Having summarised compositions according to the present invention and described preferred embodiments, specific embodiments thereof will now be described in more detail by way of example only.

EXAMPLES

In Comparison A and Examples 1 to 3, the leaching into different oils is illustrated.

The capsules E1 and E2 employed herein comprised a shell made from a complex coacervate of gelatin with respectively gum arabic or carboxymethylcellulose, cross linked with glutaraldehyde surrounding a liquid core comprising a complex mixture of perfume components comprising limonene, linalool, α-methyl ionone, lilial, hexyl salicylate and ethylene brassylate. Similar encapsulates to E1 can be made in accordance with the process in WO2006056096 and to E2 in U.S. Pat. No. 6,106,875 respectively. The characteristics of capsules E1 and E2 are summarised below.

| Encapsulate | E1 | E2 |
|---|---|---|
| Wt % Core oil/fragrance | 85/40 | 80/80 |
| Particle Size D[4, 3] | 48.4 μm | 50.7 μm |
| Measured Shell Thickness | 0.3-0.65 μm | 0.25-0.6 μm |
| DR | 58:1-40:1 | 100:1-60:1 |
| Hysitron Hardness | 4.05 MPa | 4.88 MPa |
| Apparent Reduced Elastic Modulus | 24.1 MPa | 27.5 MPa |

Mean Particle Size: D[4,3] of the capsules after dispersion in volatile silicone (cyclopentadimethicone) was obtained using a Malvern Mastersizer 2000, the following parameters.

RI of Dispersant=1.397

Dispersion module mixer speed=2100 rpm.

Result calculation model=General purpose.

Calculation sensitivity=Normal.

Particle shape=Spherical

The shell thickness for E1 was measured for particles of 19-38 μm diameter and for E2 of 25-35 μm diameter.

DR is the ratio of av. particle diameter: measured shell thickness.

The hardness (Hysitron Hardness) and Apparent Reduced Elastic Modulus herein are those measured by the following method:—

A drop of a dispersion of the capsules in demineralised water is placed onto a piece of silicon wafer and allowed to dry leaving behind discrete micro encapsulates for mechanical analysis.

The dried wafer is fitted into the Hysitron Tribo-indenter and spatially mapped using the optical system of the instrument to identify a perimeter around the sample.

The head of the Tribo-indenter is fitted with a Berkovich tip, a three sided pyramid, which compresses individual capsules. A single capsule is positioned directly under the Indenter tip. The instrument is programmed to perform an indent by compressing the sample with an initial contact force of 75 μN, for 10 seconds, followed by a position hold stage for 1 second and a decompression stage for 10 seconds. The instrument achieves a very small load (typically around 15-30 μN). The Hysitron Hardness (H in MPa) and reduced Elastic Modulus (Er in MPa) are calculated from the relaxation stage of the force deflection data using the following equations.

$$H = \frac{W}{A}$$

W=Compressive force
A=Contact Area (A≈24.56 $h_c^2$)

$$Er = \frac{\sqrt{\pi}}{2\gamma} \frac{S}{\sqrt{A}}.$$

S=Contact Stiffness (dW/dh$_t$)
h$_t$=Total Penetration Depth
γ=1.034

$$h_c = h_t - \kappa \frac{W}{S}$$

K=¾
h$_c$=Contact Depth

Results are averages of a minimum of 20 measurements made on capsules with a particle size of D[4,3]+/−20%.

The capsules, (2.5 g for E1 and 1.25 g for E2), were suspended in the respective oil or oil blend (total suspension weight of 100 g) in a set of sealed glass jars by gently shaking until a homogeneous mixture was obtained. Each sealed jar was stored in a temperature controlled chamber at 45° C. until the concentration of the representative fragrance materials in the oils in that jar was measured. One jar was measured at the start of the trial and a new jar from the set was freshly opened after the interval during the storage period stated in the Tables below. The encapsulates were separated from the carrier oil using a syringe filter fitted with a 2 μm Nylon Membrane. The separated, encapsulate-free carrier oil or oils was analysed by Gas Chromatography Mass Spectrometry (GCMS) employing 5% w/w solution of the sample and standards in ethanol, using the GCMS full scan mode. The carrier gas was helium. The identification of the representative fragrance components employed 6 peaks across the spectrum that identified those components and were discernible irrespective of the carrier oil(s). The extent of leaching calculated by comparison in a conventional way of the measured peaks and the standards. The results are tabulated below.

Comparison A and Examples 1 to 3 employed encapsulate E1.

The oil in Comparison A was a volatile silicone oil, DC245™ obtainable from Dow Corning Inc.

| Fragrance material | Comp A | Ex 1 | Ex 2 | Ex 3 |
|---|---|---|---|---|
| | Oil Composition | | | |
| | Vol sil | ester | ether | mixture |
| | % Extent of leaching after 12 weeks | | | |
| Limonene | 19 | 1 | 1 | 3 |
| Linalool | 71 | 0 | 3 | 2 |
| α-methyl ionone | 8 | 2 | 1 | 5 |
| Lilial | 14 | 1 | 0 | 3 |
| hexyl salicylate | 15 | 3 | 1 | 4 |
| ethylene brassylate | 9 | 2 | 3 | 3 |

The oil in Comparison A was a volatile silicone oil, DC245™ obtainable from Dow Corning Inc.

The oil in Example 1 was $C_{12-15}$ Alkyl Benzoate, obtainable under the tradename Finsolv TN from Finetex.

The oil in Example 2 was the INCI named material PPG-14-butyl ether available from Amerchol under the tradename Fluid AP.

In Example 3, the oil was a blend of oils was employed consisting of the volatile silicone oil, DC245, the $C_{12-15}$ Alkyl Benzoate, Finsolv TN, and the INCI named material PPG-14-butyl, Fluid AP in a weight ratio of 54.2:28.1:17.8.

From Comparison A, it is self-evident that the fragrance materials suffered from leaching into the carrier oil, especially linalool and to a noticeable extent limonene and lilial. Also the different in the extent and rate of leaching between the fragrance components is so great as to alter the balance of the residual fragrance within 12 weeks From each of Examples 1 to 3, it can be observed that the average extent of leaching of the fragrance materials was much less than in Comparison 1 and the marked extensive disparity between linalool and the remaining representative fragrances did not exist to any substantial extent.

Comparison B and Example 4

Comparison B and Example 4 repeated Comparison A and Example 3 respectively, but employing encapsulate E2.

| Fragrance material | Comp B | Ex 4 |
|---|---|---|
| | Oil composition | |
| | Vol sil | mixture |
| | % Extent of leaching after 12 weeks | |
| Limonene | 14 | 11 |
| Linalool | 19 | 12 |
| α-methyl ionone | 21 | 14 |
| Lilial | 26 | 10 |
| hexyl salicylate | 35 | 15 |
| ethylene brassylate | 29 | 13 |

Example 4 demonstrates a reduction in the rate and extent of leaching of perfume components from encapsulate E2 compared with Comparison B.

In the following Examples the ingredients employed are as follows:—

| Ingredient | Name or Trade Name | Supplier |
|---|---|---|
| Cyclomethicone [1] | DC 245 | Dow Corning Inc |
| Ester oil 1 [2] | C12-15 alkyl benzoate/ Finsolv TN | Finetex |
| Ester oil 2 [3] | Isopropyl myristate/ Estol 1512 | Uniqema |
| Ester Oil 3 | 2-phenyl ethyl benzoate Finsolv SUN | Finetex |
| Ether Oil | INCI PPG-14-butyl ether/ Fluid AP | Ucon Inc |
| Dimethicone | Dow Corning Fluid 200 (350 cSt) | Dow Corning Inc |
| Branched alcohol [4] | Isostearyl alcohol/ Prisorine 3515 | Uniqema |
| Stearyl alcohol [5] | Lorol 18 | Cognis |
| Ester wax 1 [6] | Castor wax Castorwax MP80 | CasChem Inc |

-continued

| Ingredient | Name or Trade Name | Supplier |
|---|---|---|
| Ester wax 2 [7] | Alkyl stearate behenate/ Kester Wax 82N | Koster Keunen |
| Ester wax 3 | Triglyceride wax/ Synchrowax HGL-C | Croda Ltd |
| Hydrocarbon wax1 | Polyethylene/ Performalene 400 | New Phase Technologies (Baker Petrolite) |
| Hydrocarbon wax2 | Paraffin wax SP173P, | Strahl & Pitsch |
| Hydrocarbon Polymer | Styrene-ethylene/ butylene-styrene Block copolymer/ Kraton G1650E | Kraton Polymers |
| SMGA 1 | N-(2-ethyl hexanoyl)-L-glutamic acid di-n-butylamide GA-01 | Ajinomoto |
| SMGA 2 | N-lauroyl-L-glutamic acid di-n-butylamide GP1 | Ajinomoto |
| SMGA 3 | 12-hydroxystearic acid | CasChem |
| Silicone Elastomer | 10% w/w in cyclomethicone DC9040 | Dow Corning Inc |
| Fumed silica | fumed silica Cab-o-sil | Cabot |
| Layered Clay | treated hectorite/ Bentone 38 | Rheox Inc |
| Swelling Aid | Propylene carbonate | |
| ACH | Aluminium chlorohydrate Micro Dry | Reheis Inc |
| AACH | Activated aluminium chlorohydrate A296 | B K Giulini GmbH |
| AZAG | Aluminium zirconium tatrachlorohydrex-Gly Reach 908 | Reheis Inc |
| E1 | As described above | |
| E2 | As described above | |
| ES3 | Starch encapsulate | Givaudan |
| Free Fragrance | | Fragrance House |
| Propellant | Propane, butane and isobutane CAP40 | Calor Gas Ltd. |

Foot notes
[1] DC245 can be replaced wholly or partly by DC246, or DC345 ™
[2] Finsoln TN can be replaced wholly or partly by Finsolv TPP ™
[3] Estol 1512 can be replaced wholly or partly by Estol 1517 ™
[4] Prisorine 3515 can be replaced wholly or partly by Eutanol G16 ™, (Cognis)
[5] Lorol 18 can be replaced partly (up to 50%) by Lanette 16 ™ and/or Lanette 22 ™
[6] Castorwax MP80 can be replaced wholly or partly by Castorwax MP90 ™.
[7] Kester Wax 62 can be replaced wholly or partly by Kester Wax 69H.

Examples 5 to 10

In these Examples, stick products are made by filling a dispenser comprising a barrel oval in cross section having a base and an open top covered by a cap, a platform fitting snugly within the barrel at a position intermediate between the base and the top and advancement means for the platform mounted under the base, said means comprising a rotor wheel and an attached threaded spindle engaging a cooperating thread in the platform with a composition summarised in the Table below. The summarised stick compositions are made by the following general method.

The selected oil or oils are charged in the desired weight proportion into a vessel, the desired gellant or mixture of gellants in the desired weight proportion is introduced and the resultant mixture is agitated with an agitator of suitable power or by circulation through a recirculation loop, and heated until a temperature is reached at which the gellant or all the gellants have dissolved in the oils. For waxes that temperature is commonly in the range of from 75 to 90° C. For SMGAs, depending on the particular SMGA, that temperature is often from 90 to 120° C. Thereafter, the mixture is allowed to cool by 5 to 15° C. and the desired weight proportion of particulates other than the encapsulated fragrance (including particularly the antiperspirant active) are introduced with continued agitation. The mixture is cooled or allowed to cool to a temperature of about 5 to 10° C. above the normal setting temperature of the composition (which has been determined in a previous trial). Finally, with gentle agitation, the encapsulated fragrance and any non-encapsulated (free) fragrance is introduced and the still mobile composition is charged into the dispenser.

Stick Formulations

| | Example No | | | | | |
|---|---|---|---|---|---|---|
| | 5 | 6 | 7 | 8 | 9 | 10 |
| Ingredient | | | Parts by weight | | | |
| Cyclomethicone | 34.0 | 26.0 | 47.5 | 25.0 | | 37.5 |
| Ester oil 1 | 6.0 | 15.0 | | 17.5 | | 10.0 |
| Ester oil 2 | 6.0 | | | | | |
| Ester Oil 3 | | | | | 53.15 | |
| Ether Oil | 10.0 | 9.5 | 15.0 | 15.5 | | 5.0 |
| Dimethicone | | | 5.0 | 1.0 | | |
| Branched alcohol | | | | | 11.45 | 14.0 |
| Stearyl alcohol | 15.5 | 18.0 | | | | |
| Ester wax 1 | 4.0 | 3.5 | | | | |
| Ester wax 2 | | | 10.0 | | | |
| Hydrocarbon wax 1 | | 1.0 | | 8.0 | | |
| Hydrocarbon wax 2 | | | | 6.0 | | |
| Hydrocarbon Polymer | | | | | 5.9 | |
| SMGA 1 | | | | | 2.5 | |
| SMGA 2 | | | | | 2.5 | 2.5 |
| SMGA 3 | | | | | | 7.0 |
| SMGA 4 | | | | | | |
| ACH | 24.0 | | | | | |
| AACH | | | 20.0 | | | 22.0 |
| AZAG | | 24.0 | | 24.5 | 22.5 | |
| E1 | | 1.5 | 1.5 | | | 2.0 |
| E2 | 0.5 | | | 2.0 | 1.0 | |
| ES3 | | | | 0.5 | | |
| Free Fragrance | | 1.5 | 1.0 | | 1.5 | |

Examples 11 to 13 and 15 to 17

In Examples 11 and 12, soft solid or roll-on formulations are made. The soft solid formulations are charged into a dispenser having its top covered by a dome with narrow apertures. That made with a wax gellant are made by a similar process to that of the stick formulations, the amount being insufficient to produce a hard stick. That made using a silica thickening agent comprises stirring a suspension of all the ingredients in a vessel at a temperature in the range of 25 to 50° C. until an homogeneous suspension is obtained, and thereafter top filling it into the dispenser and placing the dome in the mouth.

In Example 13, a roll-on formulation is made by a similar method to Example 12, employing less thickener.

In Example 14, the roll-on formulation is absorbed into a non-woven applicator cloth.

In Examples 15 to 17, an aerosol product is made by the following general method. All the ingredients of the base composition (i.e. all except for the propellant) are blending in a vessel at ambient temperature until an homogenous mixture is obtained. Then the base composition is charged into a preformed aluminium can, a valve cup supporting a valve from which depends a dip tun=be is crimped into place, and propellant is charged into the can through the valve. Thereafter, an actuator is placed above the valve stem extending upwards from the valve.

| Ingredient | 11 | 12 | 13 | 15 | 16 | 17 |
|---|---|---|---|---|---|---|
| Cyclomethicone | 32.5 | 32.0 | 54.5 | 7.0 | 2.79 | 5.6 |
| Ester oil 1 | 14.0 | 10.0 | 15.0 | 5.0 |  | 1.0 |
| Ester oil 2 | 7.5 |  |  | 2.3 |  |  |
| Ether Oil |  | 5.0 | 10.0 |  | 3.0 |  |
| Dimethicone | 8.0 | 7.0 | 2.0 | 3.0 |  |  |
| Ester wax 3 | 3.25 |  |  |  |  |  |
| Hydrocarbon wax 2 | 3.25 |  |  |  |  |  |
| Silicone elastomer | 4.0 |  |  |  |  |  |
| Fumed silica |  | 5.0 | 1.5 | 0.4 |  |  |
| Layered Clay |  |  |  | 1.25 | 0.5 | 0.5 |
| Swelling Aid |  |  |  | 0.05 | 0.01 |  |
| ACH |  |  | 15.0 | 10.0 |  |  |
| AACH |  | 12.0 |  |  | 5.0 | 5.0 |
| AZAG | 25.0 | 12.0 |  |  |  |  |
| Propellant |  |  |  | 70.0 | 87.0 | 87.0 |
| E1 | 1.5 |  | 1.0 | 0.5 | 0.6 |  |
| E2 |  | 1.5 |  |  |  | 0.3 |
| ES3 | 0.5 | 0.5 |  |  | 0.1 |  |
| Free Fragrance | 0.5 |  | 1.0 | 0.5 | 1.0 | 0.6 |

The invention claimed is:

1. An anhydrous antiperspirant composition comprising particulate antiperspirant active, capsules of perfume, a liquid carrier oil for the particulate antiperspirant active and capsules of perfume, and a solidifying agent, the liquid carrier oil comprising water-immiscible oil that comprises (a) volatile silicone oil and (b) a material selected from the group consisting of a water-immiscible ether oil, a water-immiscible ester oil, and a blend thereof, the liquid carrier oil comprising nothing other than the water-immiscible oil wherein:

the composition is in the form of a stick or soft solid;
component (a) is from 30 to 70% by weight of the water immiscible oil and component (b) is greater than 15% by weight of said water-immiscible oil;

wherein when the liquid carrier oil comprises a water-immiscible ether oil, the water-immiscible ether oil comprises a C2 to C6 alkyl ether of a polypropylene glycol comprising from 10 to 20 propylene glycol units;

wherein when the liquid carrier oil comprises a water-immiscible ester oil, the water-immiscible ester oil comprises an aromatic ester;

wherein the capsules of perfume are water-insoluble, dry particulate friction-sensitive capsules of perfume that comprise a shell made from a complex coacervate of gelatin with gum Arabic that is cross-linked with glutaraldehyde or from a complex coacervate of gelatin with carboxymethylcellulose that is cross-linked with glutaraldehyde, wherein the capsules have an average shell thickness in the range of from 0.25 to 10 μm and a ratio of average shell thickness to average capsule diameter in the range of from 1:7 to 1:100.

2. A composition according to claim 1 in which the water-immiscible oil comprises at least 20% by weight of an aromatic ester.

3. A composition according to claim 2 in which the aromatic ester comprises an alkyl benzoate.

4. A composition according to claim 1 in which the water immiscible oil comprises at least 20% by weight of a C3 to C6 alkyl ether derivative of polypropylene oxide.

5. A composition according to claim 1 in which the water-immiscible oil comprises up to 5% by weight of a triglyceride oil.

6. A composition according to claim 1 in which the water-immiscible oil comprises up to 5% by weight of a non-encapsulated fragrance oil or mixture of fragrance oils.

7. A composition according to claim 1 which comprises from 10 to 25% by weight of the antiperspirant active, from 0.1 to 5% by weight of the water-insoluble friction-sensitive capsules of perfume, from 30 to 60% by weight of the water-immiscible oils, and from 4 to 25% by weight of the solidifying agent.

8. A composition according to claim 1 in which the fragrance material within the fragrance capsules comprises linalool or/and limonene.

9. A composition according to claim 1 which is free from ethanol.

10. A composition according to claim 1 which additionally contains a water-sensitive encapsulated fragrance.

* * * * *